United States Patent [19]

Goffman

[11] Patent Number: 4,862,902
[45] Date of Patent: Sep. 5, 1989

[54] EYE PROTECTOR

[76] Inventor: Joel H. Goffman, 8535 W. Bellfort, Houston, Tex. 77071

[21] Appl. No.: 163,957

[22] Filed: Mar. 3, 1988

[51] Int. Cl.⁴ .................... A61F 13/00; A61F 9/00
[52] U.S. Cl. .......................................... 128/858; 2/15
[58] Field of Search ............... 128/132 R, 155, 858, 128/163; 2/15, 433, 431, 432

[56] References Cited

U.S. PATENT DOCUMENTS

| | | | |
|---|---|---|---|
| 1,161,321 | 11/1915 | Lush | 2/15 |
| 1,959,915 | 5/1934 | Guthrie | 2/433 |
| 2,165,668 | 7/1939 | Vaccaro | 2/15 |
| 2,643,382 | 6/1953 | McLeod | 2/15 |
| 3,092,103 | 6/1963 | Mower | 2/15 |
| 3,339,206 | 9/1967 | Daley | 2/15 |
| 4,473,370 | 9/1984 | Weiss | 128/155 |
| 4,581,877 | 4/1986 | Wilber | 128/132 R |

*Primary Examiner*—Robert A. Hafer
*Assistant Examiner*—Michael Brown
*Attorney, Agent, or Firm*—Ben D. Tobor

[57] ABSTRACT

An eye protector, which includes a rigid shield for protecting the eye after an injury or surgery, utilize a flexible adhesion member to removably secure the rigid shield to the face of a wearer.

10 Claims, 1 Drawing Sheet

U.S. Patent  Sep. 5, 1989  4,862,902
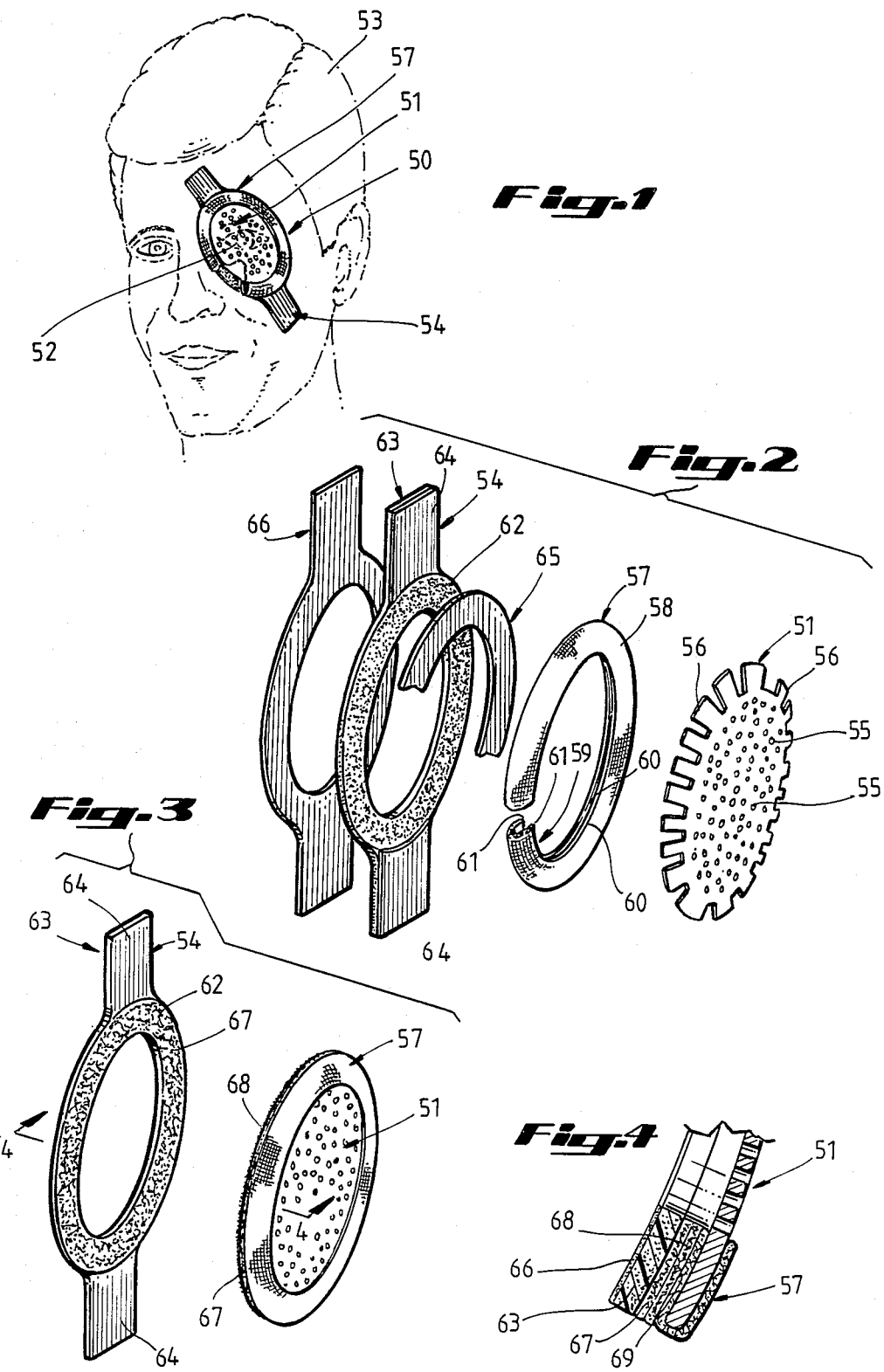

EYE PROTECTOR

FIELD OF THE INVENTION

The invention relates to eye protection devices, in particular those adapted to protect the eye from blunt trauma.

DISCUSSION OF THE PRIOR ART

Eye shields have been used for many years to protect the eye at times when it is especially susceptible to injury from impact. For example, shields are commonly used to protect the eye allowing it to heal following an injury or after surgery. For example, eye surgery, such as cataract removal, usually requires that the affected eye be covered with a suitable, protective pad during the recovery period which can often times last several weeks or more. Various devices are known in the prior art for this purpose. However, as is well known in the art, such eye protectors have had many disadvantages and many problems associated therewith.

One of the major problems associated with the presently used eye protectors or eye shields has been the means for attaching the eye shield over the injured eye of the wearer to hold the shield accurately and securely in position. Many of the presently used eye shields are held in position by elastic bands or straps or a harness of straps which fit across the forehead and around the head of the wearer. These devices are often cumbersome and uncomfortable to the wearer, and may even cause further injury to the eye of the wearer. This is due to the tendency of the straps to slip, interfering with the proper vision of the other eye, and causing the eye shield itself to move toward, or upon, the eye, thus creating pressure on the injured eye. Such contact and-/or pressure causes stress on a post-operative eye and risk of the potential rupturing or opening of any incisions made therein. Another means for attaching an eye shield over an injured or post-operative eye has been to use certain surgical adhesive tape which, as is well known, is extremely painful and difficult to remove, at times actually taking the skin off the patient with the tape.

In addition to the drawbacks previously noted, the surgical adhesive tape that is typically used as a means of attaching the eye shields or eye protectors around the eye of the post-operative patient is very difficult to keep clean. There is a problem in keeping the surfaces which contact the wearer's skin sufficiently clean to avoid irritation and possible infection. Further drawbacks of the eye protectors known in the prior art are the relative expense in manufacturing.

Numerous eye protectors and means of attachment have been proposed over the years to solve the foregoing described problems and disadvantages. However, in general, such devices have not met with much success in solving the foregoing described problems and disadvantages. Typically, such prior art eye protectors and attachment means have required the use of an extremely uncomfortable rigid disk held in position with either straps, which could possibly further injure the eye as described, or surgical adhesive tape, which is extremely difficult and painful to remove. Also, as most post-operative eye patients wear eye shields for several weeks or more, surfaces which contact the wearer's skin become very dirty and unsightly, causing irritation and a possible risk of infection. In general, such prior art eye protector devices are cumbersome and uncomfortable for the wearer to use, and cause a risk of further injury to the eye itself or the surrounding facial area.

Accordingly, prior to the development of the present invention, there has been no eye protector device adapted to protect the eye from blunt trauma which: provides a maximum degree of comfort, is convenient and easy to use, and easily secured to the face of the wearer; may be easily attached and removed from the eye of the wearer without causing pain or further injury; prevents improper contact or pressure being applied to the eye; is easily kept clean, thus avoiding unsightliness, undue irritation, and possible infection to the wearer; and is simple and economical to use.

Therefore, the art has sought an eye protection device adapted to protect the eye from blunt trauma which: provides a maximum degree of comfort, is convenient and easy to use, and easily secured to the face of the wearer; may be easily attached and removed from the eye of the wearer without causing pain or further injury; prevents improper contact or pressure from being applied to the eye; is easily kept clean, thus avoiding unsightliness, undue irritation, and possible infection; and is simple and economical to use.

SUMMARY OF THE INVENTION

In accordance with the invention the foregoing advantages have been achieved through the present eye protector adapted to protect the eye from blunt trauma. The present invention includes: a generally oval-shaped, rigid member adapted to cover the eye of the wearer; and a flexible adhesion member having front and rear adhesion surfaces, the rigid member being removably secured to the front adhesion surface and the rear adhesion surface being adapted to be removably secured to the wearer; the adhesion member being sufficiently flexible to conform to the facial contours of the wearer whereby the eye of the wearer is protected.

A feature of the present invention resides in the fact that the flexible adhesion member may be substantially oval-shaped, having an opening formed in the center thereof to permit sight and two elongated tab members disposed at opposite ends of the adhesion member. Another feature of the present invention is that the oval-shaped, rigid member may include a plurality of apertures sized to permit sight and a plurality of deformable portions about the periphery thereof, whereby the peripheral portion of said protector may be deformed to conform to the facial contours of the wearer. A further feature of the present invention is that the eye protector may include a cover member detachably mounted about the periphery of the rigid member and overlying the deformable portions, which cover member may further include a fabric cover and elastic means for maintaining the fabric cover about the periphery of the rigid member.

In accordance with the invention the foregoing advantages have also been achieved through a flexible adhesion member in accordance with the present invention. The flexible adhesion member may include an elongate member having front and rear adhesion surfaces, a rigid member being removably secured to the front adhesion surface and the rear adhesion surface being adapted to be removably secured to the wearer, the adhesion member being sufficiently flexible to conform to the facial contours of the wearer, whereby the eye of the wearer is protected.

The eye protector, adapted to protect the eye from blunt trauma, of the present invention when compared with previously proposed prior art eye protector devices has the advantages of: providing a maximum degree of comfort, being convenient and easy to use and easily secured to the face of the wearer; being easily attached and removed from the eye of the wearer without causing pain or further injury; preventing improper contact or pressure being applied to the eye; being easily kept very clean, thus avoiding unsightliness, undue irritation, and possible infection to the wearer; and being simple and economical to use.

BRIEF DESCRIPTION OF THE DRAWING

In the Drawing:

FIG. 1 is a perspective view illustrating the use of an eye protector in accordance with the present invention; and FIG. 2 is an exploded, perspective view of an eye protector in accordance with the present invention; and FIG. 3 is an exploded, perspective view of an eye protector in accordance with the present invention; and FIG. 4 is a cross-sectional view of an eye protector taken along line 4—4 of FIG. 3 in accordance with the present invention.

The invention will be described in connection with the preferred embodiment, and it will be understand that it is not intended to limit the invention to that embodiment. On the contrary, it is intended to cover all alternatives, modifications, and equivalents as may be included within the spirit and scope of the invention and defined by the appended claims.

DETAILED DESCRIPTION OF THE INVENTION

In FIG. 1, an eye protector 50 in accordance with the present invention is shown to generally comprise: a generally oval-shaped, rigid member 51 adapted to cover the eye 52 of a wearer 53; a flexible adhesion member 54 having front and rear adhesion surfaces to be hereinafter described in greater detail. The oval-shaped, rigid member 51 may be formed from a rigid, plastically deformable and preferably light-weight material, such as aluminum or any suitable plastic material having the requisite rigidity and deformability characteristics.

With reference to FIG. 2, the oval-shaped, rigid member 51 preferably includes a plurality of apertures 55 sized to permit sight and a plurality of deformable portions, or bendable tabs 56, disposed about the periphery of member 51. The peripheral portion of rigid member 51 formed by the deformable, or bendable, tabs 56 may thus be deformed to conform to the facial contours of the wearer 53. An annular cover member 57 may be detachably mounted about the periphery of the rigid member 51 and overlying the deformable portions 56. The cover member 57 is preferably formed of a fabric cover 58 and elastic means for maintaining 59 the fabric 58 about the periphery of the rigid member 51. Preferably the elastic means 59 comprises a length of elastic material 60 sewn into each of the interior surfaces 61 of cover member 57.

With reference now to FIGS. 2 and 3, the flexible adhesion member 54 has front and rear adhesion surfaces, 62,63. The rigid member 51 can be removably secured to the front adhesion surface 62, and the rear adhesion surface 63 can be adapted to be removably secured to the wearer. The adhesion member 54 is sufficiently flexible to conform to the facial contours of the wearer. The adhesion member 54 has an oval shape which mates with the oval-shaped, rigid member 51. The adhesion member 54 also includes two elongated tab members 64, having front and rear surfaces, disposed on opposite ends of adhesion member 54. Before use and while in storage, the front and rear adhesion surfaces 62,63 of adhesion member 54 are protected with protective strips of material 65,66 with a low degree of adhesion, such as a waxy paper or similar low adhering materials.

With reference to FIG. 2, the rear adhesion surface 63 of the oval-shaped adhesion member 54 and the rear of the adhesion tabs 64 may be formed of a polyethylene foam tape maintaining the adhesion member 54 around the eye 52 and upon the face of the wearer 53. The front adhesion surface 62 may be formed of a transparent polyester tape maintaining the rigid member 51 on the adhesion member 54. The rigid member 51 may be removably secured to the adhesion member 54 with or without the cover member 57. It should be noted that the adhesive utilized on the rear adhesion surface should be able to sufficiently stick on, or remain fast to, the skin of the wearer, while also permitting easy removal of the adhesion member 54 and tabs 64, when desired, without harming the skin of the wearer.

With reference now to FIGS. 3 and 4, the front adhesion surface 62 may alternatively be formed of a velcro type material, such as a nylon material made with a surface of tiny hooks 67, which mates with a complementary surface of an adhesive pile 68. The cover member 57 about the periphery of the rigid member 51 would then be formed of a fabric cover with a velcro type pile material 68 sewn onto the exterior rear surface 69 of cover member 57 that would mate with the front adhesion surface 62.

It is to be understood that the invention is not to be limited to the exact details of construction, operation, exact materials, or embodiment shown and described as modifications and equivalents will be apparent to one skilled in the art. Accordingly, the invention is to be limited only by the scope of the appended claims.

I claim:

1. An eye protector comprising:
 a generally oval-shaped, convexo-concave formaminous rigid number adapted to cover the eye of a wearer and having a plurality of apertures disposed therein and sized to permit sight, and a plurality of bendable tabs forming the periphery of the rigid member and extending radially outwardly therefrom, whereby the peripheral portion of the rigid member may be deformed to conform to the facial contours of the wearer; and
 a flexible adhesion member having front and rear adhesion surfaces, the periphery of the rigid member formed by the plurality of bendable tabs being removably secured to the front adhesion surface and the rear adhesion surface being adapted to be removably secured to the wearer, the adhesion member being sufficiently flexible to conform to the facial contours of the wearer, whereby the eye of the wearer is protected.

2. The eye protector as in claim 1, wherein the adhesion member has an oval shape which mates with the oval shape of the rigid member, and two elongated tab members, having front and rear surfaces disposed on opposite ends of the adhesion member.

3. The eye protector of claim 2, wherein the rear adhesion surface of the oval-shaped adhesion member and adhesion tabs are a polyethylene foam tape maintaining the adhesion member around the eye and upon the face of the wearer.

4. The eye protector of claim 2, wherein the front adhesion surface of the oval-shaped adhesion member is transparent polyester tape maintaining the rigid member on the adhesion member.

5. The eye protector of claim 2, wherein the front adhesion surface of the oval-shaped adhesion member is a velcro type material maintaining the rigid member on the adhesion member.

6. The eye protector of claim 2, wherein the adhesion member includes an opening formed in the center of the oval shape to permit sight.

7. The eye protector of claim 1, further comprising a cover member detachably mounted about the periphery of the rigid member and overlying the deformable portions.

8. The eye protector of claim 7, wherein the cover member includes a fabric cover and elastic means for maintaining the fabric cover about the periphery of the rigid member.

9. The eye protector of claim 1, wherein said rigid member and said deformable portion comprises a single place of rigid, plastically deformable material.

10. An eye protector, comprising:
a substantially oval-shaped rigid member having a concave cross-section, a plurality of bendable tabs extending radially about the periphery thereof, and a plurality of apertures formed therein and sized to permit sight;
a fabric cover about the periphery of the rigid member overlying said bendable tabs;
a substantially oval-shaped flexible adhesion member having an opening formed in the center thereof and two elongated tab members disposed at opposite ends of the adhesion member and having front and rear adhesion surfaces, the rigid member being removably secured to the front adhesion surface and the rear adhesion surface being adapted to be removably secured to a wearer.

* * * * *